(12) United States Patent
Yamada

(10) Patent No.: US 8,086,061 B2
(45) Date of Patent: Dec. 27, 2011

(54) IMAGE PROCESSING DEVICE AND IMAGE PROCESSING METHOD

(75) Inventor: Naoki Yamada, Soka (JP)

(73) Assignee: Canon Kabushiki Kaisha, Tokyo (JP)

( * ) Notice: Subject to any disclaimer, the term of this patent is extended or adjusted under 35 U.S.C. 154(b) by 692 days.

(21) Appl. No.: 12/253,544

(22) Filed: Oct. 17, 2008

(65) Prior Publication Data

US 2009/0103826 A1 Apr. 23, 2009

(30) Foreign Application Priority Data

Oct. 22, 2007 (JP) ................................. 2007-273513

(51) Int. Cl.
*G06K 9/40* (2006.01)
*G01N 23/04* (2006.01)

(52) U.S. Cl. ......................................... 382/254; 378/62
(58) Field of Classification Search .................. 382/254, 382/128–132; 378/62, 4, 19, 98.8, 98.11, 378/98.12
See application file for complete search history.

(56) References Cited

U.S. PATENT DOCUMENTS

| 5,210,688 | A | * | 5/1993 | Cheu et al. ....................... 378/19 |
| 5,748,768 | A | * | 5/1998 | Sivers et al. .................... 382/130 |
| 7,601,962 | B2 | * | 10/2009 | Petrick et al. ............. 250/370.09 |
| 2006/0188061 | A1 | | 8/2006 | Takenaka et al. |
| 2008/0049900 | A1 | | 2/2008 | Takenaka et al. |

FOREIGN PATENT DOCUMENTS

JP 2006-267093 A 10/2006

* cited by examiner

*Primary Examiner* — Irakli Kiknadze

(57) ABSTRACT

An image-data reading unit reads image data stored after radiation irradiation is performed from a radiation detector. An offset-data reading unit reads offset data in a case in which no radiation irradiation is performed from the radiation detector. After radiation irradiation is performed, a drive control section drives the image-data reading unit so that the image-data reading unit reads image data. Then, the drive control section drives the offset-data reading unit so that the offset-data reading unit reads offset data before the next irradiation is performed. In a period in which radiation irradiation is not performed, the image data and the offset data that have been read are sent to an image-handling section. The image data and the offset data that have been received by a data sending/receiving unit are subjected to subtraction processes by an image processing unit.

6 Claims, 5 Drawing Sheets

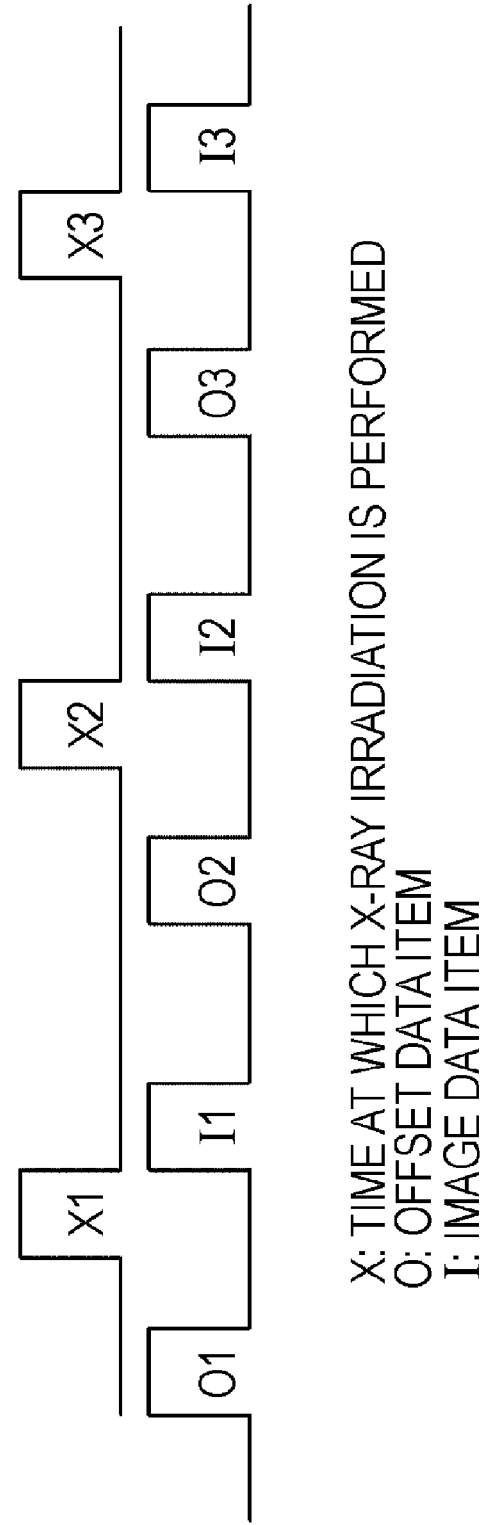

IMAGE PROCESSING DEVICE AND IMAGE PROCESSING METHOD

BACKGROUND OF THE INVENTION

1. Field of the Invention

The present invention relates to an image processing device and an image processing method for correcting an image data item using an offset data item in a radiation image processing field.

2. Description of the Related Art

In a radiograph apparatus in which a radiation detector is mounted, in order to reduce noise that occurs due to the characteristics of the radiation detector, noise correction is performed using an offset data item. The offset data item is a data item that is read from the radiation detector when radiation irradiation is not performed, and is referred to as a dark current or a dark image. A noise correction method is performed by subtracting the offset data item from an image date item. In other words, the offset data item obtained by reading only noise is subtracted from an image data in which noise exists, thereby performing noise correction.

Japanese Patent Laid-Open No. 2006-267093 discloses a method for reading an offset data item shown in FIG. 5. In the method shown in FIG. 5, each time that an image data item is read, an offset data item is read before and after the image data item is read. An offset data item that is read before an image data item is read is referred to as a "pre-offset data item". An offset data item that is read after the image data item has been read is referred to as a "post-offset data item". For example, O2 denotes a pre-offset data item for an image data item I2, and O3 denotes a post-offset data item for the image data item I2. X1, X2, and X3 denote each a time at which X-ray irradiation is performed.

Typically, a noise correction process using an offset data item is performed using a post-offset data item. The reason for this is that an afterimage of an image of the previous frame exists in a pre-offset data item, and, when the pre-offset data item is subtracted from an image data item, the image data item is influenced by the afterimage.

In other words, referring to FIG. 5, to correct the image data item I2, a subtraction process represented by (I2−O2) may be performed. However, in such a case, because an afterimage of an image data item I1 exists in the pre-offset data item O2, the afterimage of the image data item I1 influences the image data item I2, although the influence is small. In contrast, a subtraction process represented by (I2−O3) may alternatively be performed. In this case, only an afterimage of the image data item I2 exists in the post-offset data item O3. Accordingly, the negative influence of the afterimage is smaller and the quality of an image is higher than that of an image corrected by the subtraction process represented by (I2−O2).

However, in the correction process using a post-offset data item, a time taken to obtain a post-offset data item is necessary after an image data item has been obtained. Thus, a time taken from when the image data item is obtained to when the image data item is displayed is longer than that taken in a case in which the image data item is corrected using a pre-offset data item.

Additionally, as described above, when the correction process using a pre-offset data item is performed, a time taken until an image data item is displayed is short. However, the quality of an image is lower than that of an image which is corrected using a post-offset data item.

In addition, in a case of image diagnostic in the medical field, a higher-quality image frequently is necessary so that a small tumor or the like can be found by checking the image.

Furthermore, in a moving-image-pickup apparatus using radiation, a current or voltage value that is necessary in order to generate radiation while an image is being picked up is controlled using image analysis. Accordingly, in order to perform the image analysis with a high accuracy, it is important to obtain a high-quality image.

In the medical field, in particular, displaying of an image in real time is advantageous to a case in which the moving-image-pickup apparatus using radiation is used in an operation. For example, when a manipulation in which a catheter is inserted into a human body is performed, while a doctor is irradiating the human body with radiation, an image data item obtained as a result of the irradiation is displayed on a monitor. The doctor continues inserting the catheter while checking the displayed image. In such a case, when there is a time difference between insertion of the catheter and corresponding display of the image, there is a risk that the doctor moves the catheter in a wrong direction. Thus, displaying of the image in real time is important.

SUMMARY OF THE INVENTION

The present invention has been made in consideration of the above situation. The present invention provides an image processing device and an image processing method capable of obtaining a high-quality radiation image with a high accuracy.

According to an aspect of the present invention, an image processing device in a radiograph apparatus includes a radiation detector, an image-data reading section configured to read an image data item stored in the radiation detector, an offset-data reading section configured to read offset data items from the radiation detector in a period in which radiation irradiation is not performed, and a control section configured to control the image-data reading section and the offset-data reading section. The image processing device includes the following elements: a data sending/receiving unit configured to send/receive data items from the image-data reading section and the offset-data reading section; an image processing unit configured to generate a first image data item by subtracting a first offset data item read by the offset-data reading section from the image data item read by the image-data reading section, the first offset data item read before the image data item is read, and configured to generate a second image data item by subtracting a second offset data item read by the offset-data reading section from the image data item read by the image-data reading section, the second offset data item read after the image data item is read; a display unit configured to display the first image data item generated by the image processing unit; and a storage unit configured to store the second image data item generated by the image processing unit.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

FIG. 5 illustrates offset-data read timing according to a conventional method.

DESCRIPTION OF THE EMBODIMENTS

Various embodiments of the present invention are described in detail below with reference to the accompanying drawings.

First Embodiment

Figure 1:
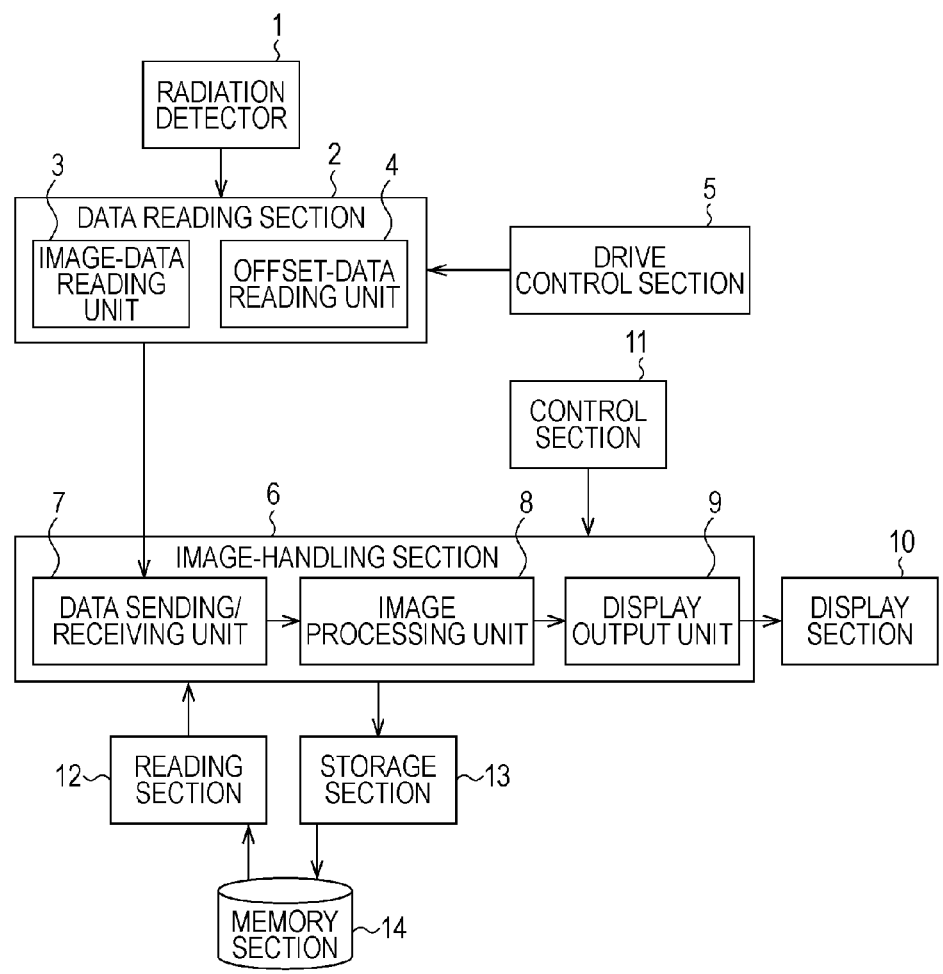
FIG. 1 is a block diagram of a circuit configuration of an image processing device according to a first embodiment of the present invention.

FIG. 1 is a block diagram of a circuit configuration of an image processing device according to a first embodiment of the present invention. An output of a radiation detector 1, which detects radiation that has been emitted from a radiation generating apparatus (not illustrated), is connected to a data reading section 2. The data reading section 2 includes an image-data reading unit 3 and an offset-data reading unit 4, and an output of a drive control section 5 is connected to the data reading section 2. Additionally, an output of the data reading section 2 is connected to a data sending/receiving unit 7 provided in an image-handling section 6. The image-handling section 6 includes the data sending/receiving unit 7, an image processing unit 8, and a display output unit 9. An output of the data sending/receiving unit 7 is connected to the image processing unit 8, and the display output unit 9 in this order, and an output of the display output unit 9 is connected to a display section 10. Furthermore, outputs of a control section 11 and a reading section 12 are connected to the image-handling section 6, and an output of the image-handling section 6 is connected to a storage section 13. An output of the storage section 13 is connected to a memory section 14, and an output of the memory section 14 is connected to the reading section 12.

The image-data reading unit 3 reads an image data item that is stored after radiation irradiation is performed from the radiation detector 1. The offset-data reading unit 4 reads an offset data item in a case in which radiation irradiation is not performed from the radiation detector 1.

After radiation irradiation is performed, the drive control section 5 drives the image-data reading unit 3 so that the image-data reading unit 3 reads an image data item. After reading of the image data item by the image-data reading unit 3 is finished, the drive control section 5 drives the offset-data reading unit 4 so that the offset-data reading unit 4 reads an offset data item before the next irradiation is performed. A drive control method performed by the drive control section 5 is not necessarily limited to the above-described method. A method for continuously driving the offset-data reading unit 4 a plurality of times may be used.

An image data item and offset data items that have been read by the data reading section 2 are sent to the image-handling section 6 in a period in which radiation irradiation is not performed. The image data item and the offset data items that have been received by the data sending/receiving unit 7 are subjected to subtraction processes by the image processing unit 8. In other words, the subtraction processes are performed by the image processing unit 8 for both offset data items, i.e., a pre-offset data item and a post-offset data item. The offset data items are subtracted from the image data item, thereby performing noise correction processes.

In other words, when the subtraction processes are described with reference to FIG. 5 that is described above, the image processing unit 8 performs two subtraction processes for an image data item I2: a first image data item (I2−O2) is generated using a pre-offset data item O2; and a second image data item (I2−O3) is generated using a post-offset data item O3.

The image data items obtained by the noise correction processes performed by the image processing unit 8 are each displayed on the display section 10 by the display output unit 9, or stored in the memory section 14 by the storage section 13.

The image data item that is stored in the memory section 14 can be read again by the reading section 12. Additionally, the image data item that has been read again can be displayed on the display section 10 via the display output unit 9 of the image-handling section 6.

The control section 11 controls operation of the image-handling section 6. In other words, from among the image data items that have been processed by the image processing unit 8, the image data item obtained by performing the correction process using the pre-offset data item is sent to the display output unit 9, and displayed on the display section 10. In contrast, from among the image data items that have been processed by the image processing unit 8, the image data item obtained by performing the correction process using the post-offset data item is sent to the storage section 13, and stored in the memory section 14.

The control section 11 performs the above-described control for the image-handling section 6, whereby an image obtained by correcting the image data item using the pre-offset data item can be immediately displayed, and whereby a high-quality image obtained by correcting the image data item using the post-offset data item can be stored. Furthermore, image analysis is performed for the high-quality image by the image processing unit 8. A current or voltage value that has been calculated using the image analysis can be fed back to the radiation generating apparatus (not illustrated).

Second Embodiment

Figure 2:
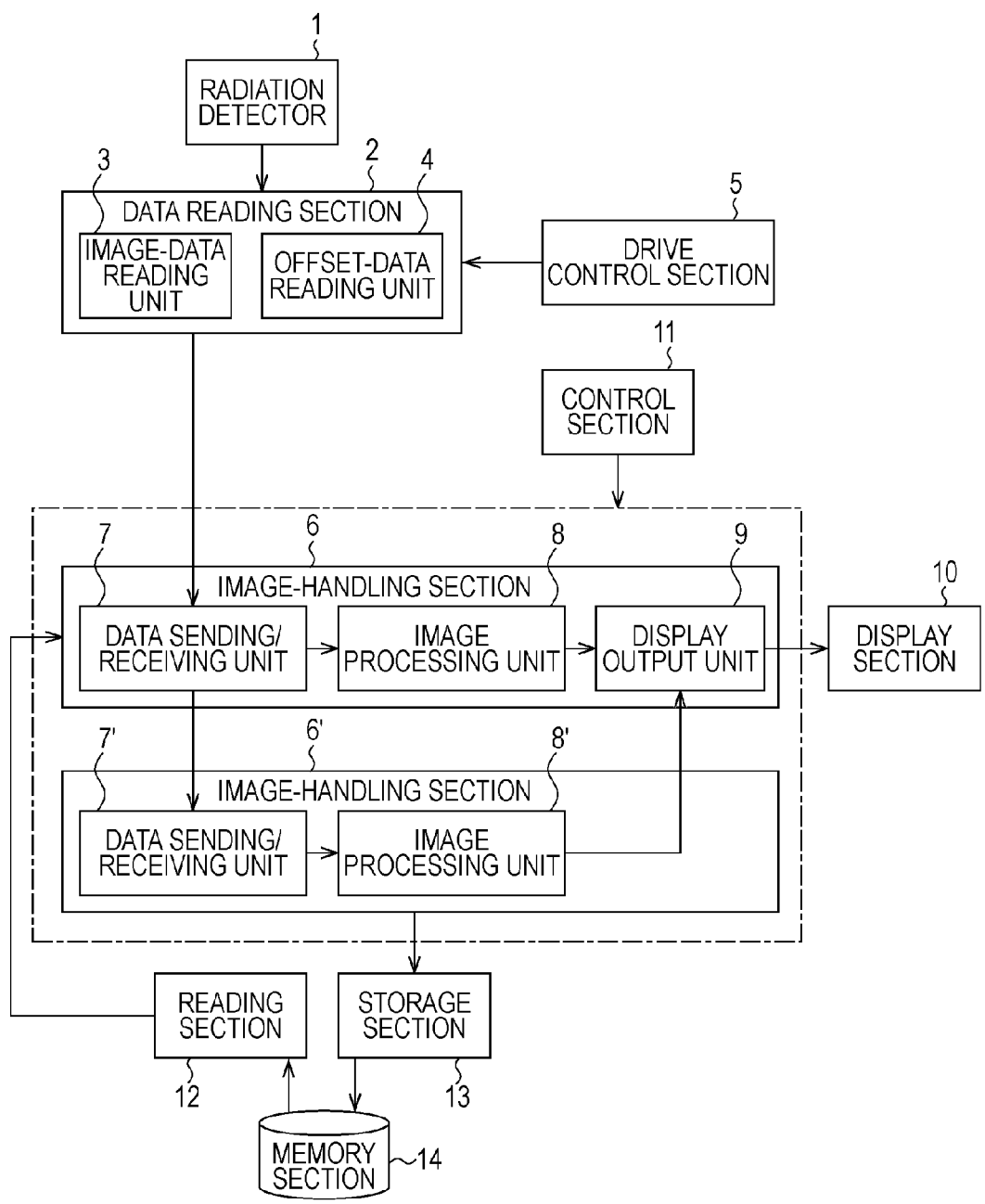
FIG. 2 is a block diagram of a circuit configuration of an image processing device according to a second embodiment of the present invention.

FIG. 2 is a block diagram of a circuit configuration of an image processing device according to a second embodiment. The elements denoted by reference numerals the same as those used in the first embodiment have the same functions. The difference between the second embodiment and the first embodiment is the existence of an image-handling section 6', which is additionally provided. In other words, referring to FIG. 2, two image-handling sections 6 and 6' exist, and an output of the data sending/receiving unit 7 of the image-handling section 6 is connected to a data sending/receiving unit 7' of the image-handling section 6'. Additionally, an output of the image-handling section 6 is connected to the display section 10, and an output of the image-handling section 6' is connected to the storage section 13. The output of the reading section 12 is connected to the image-handling section 6.

As described in the first embodiment, the data sending/receiving unit 7 receives an image data item and offset data items from the data reading section 2. In the first embodiment, the image processing unit 8 performs the two correction processes, i.e., the correction process using a pre-offset data item and the correction process using a post-offset data item. However, in the second embodiment, the image processing unit 8 performs only the correction process using a pre-offset data item. In other words, when the data sending/receiving unit 7 receives an image data item and offset data items, the image processing unit 8 subtracts a pre-offset data item for the received image data item from the received image data item. The image data item obtained by the subtraction is displayed on the display section 10 by the display output unit 9.

Furthermore, when the data sending/receiving unit 7 receives the image data item and the offset data items from the data reading section 2, the data sending/receiving unit 7 sends only the image data item and a post-offset data item for the image data item to the data sending/receiving unit 7' of the image-handling section 6'. Then, the data sending/receiving unit 7' receives the two data items.

When the data sending/receiving unit 7' receives the image data item and the post-offset data item for the image data item, the data sending/receiving unit 7' sends the data items to an image processing unit 8'. Then, the image processing unit 8' subtracts the post-offset data item for the image data item from the image data item, and the image data item obtained by the subtraction is stored in the memory section 14 by the storage section 13.

The image data item that is stored in the memory section 14 is read by the reading section 12, and is passed to the image-handling section 6. Then, the image data item can be displayed again on the display section 10 by the display output unit 9.

In this manner, referring to FIG. 2, the correction process using the pre-offset data item and the correction process using the post-offset data item can be separately performed by the two image-handling sections 6 and 6', resulting in improvement of the system throughput.

Third Embodiment

Figure 3:
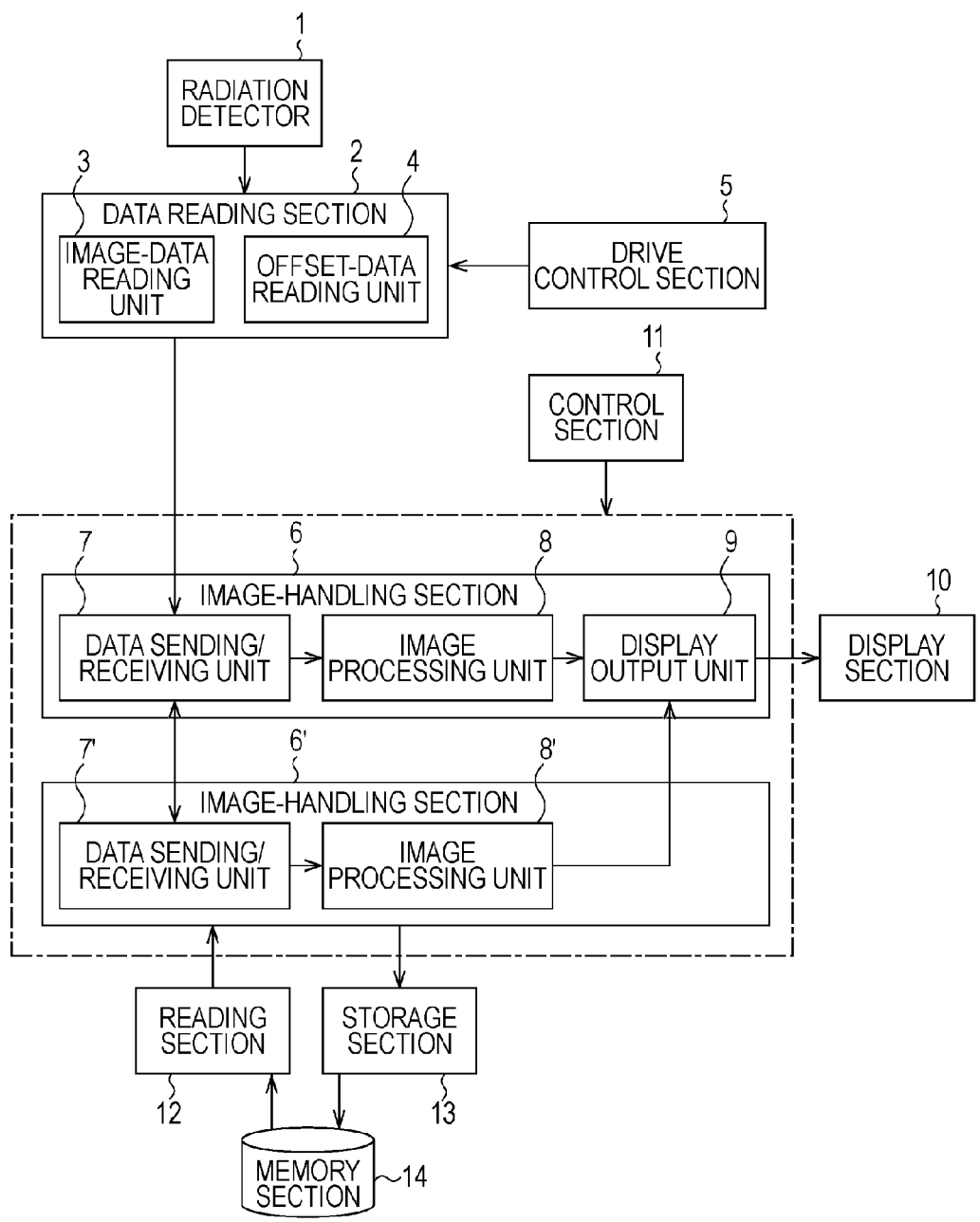
FIG. 3 is a block diagram of a circuit configuration of an image processing device according to a third embodiment of the present invention.

FIG. 3 is a block diagram of a circuit configuration of an image processing device according to a third embodiment. The difference between the third embodiment and the second embodiment is that data items can be bidirectionally sent/received between the data sending/receiving units 7 and 7', and that an image data item that has been read from the memory section 14 is passed to the image-handling section 6'.

The image data item that has been passed to the image-handling section 6' is sent to the data sending/receiving unit 7 of the image-handling section 6 by the data sending/receiving unit 7'. The image data item that has been received by the data sending/receiving unit 7 can be displayed again on the display section 10 by the display output unit 9.

Fourth Embodiment

Figure 4:
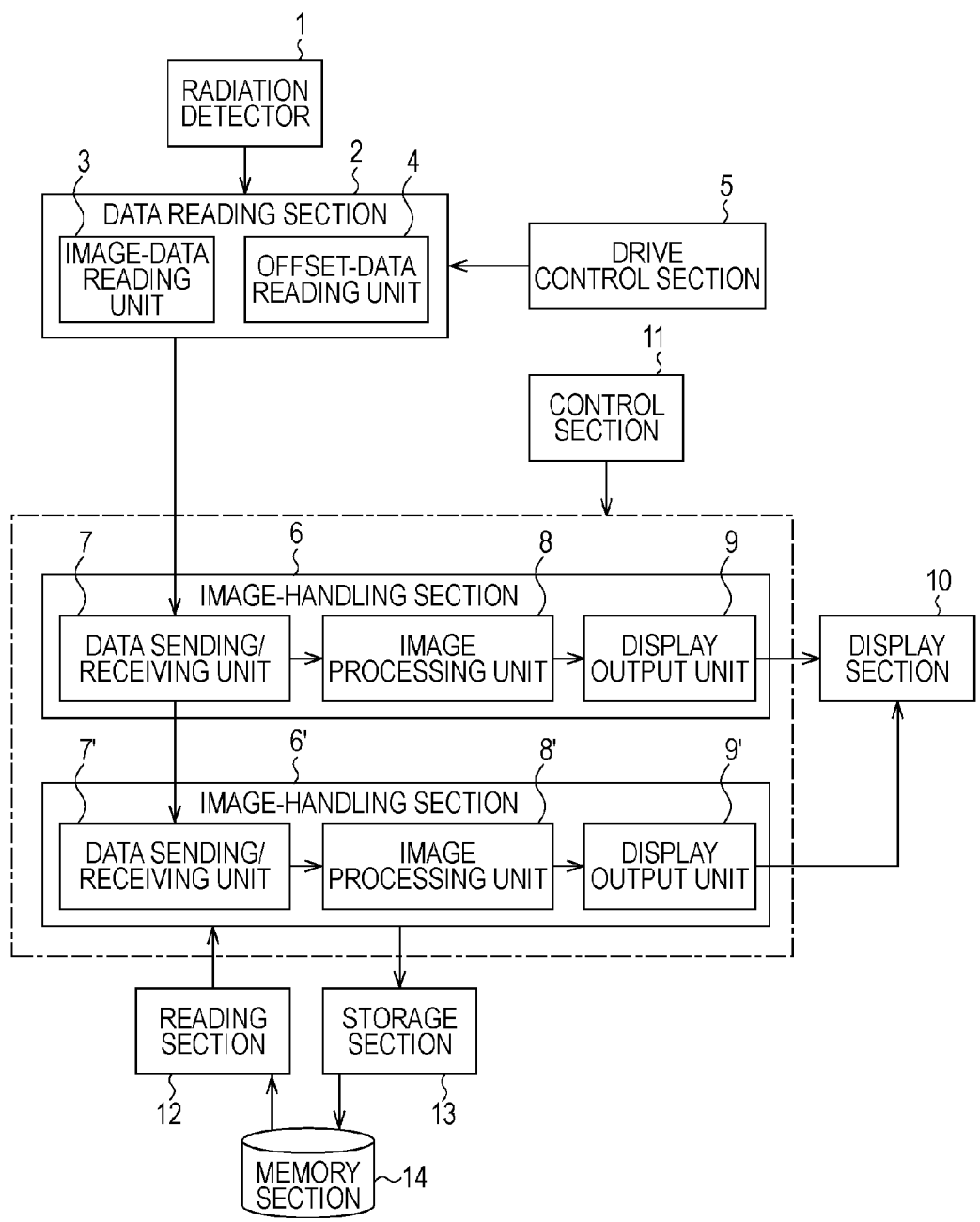
FIG. 4 is a block diagram of a circuit configuration of an image processing device according to a fourth embodiment of the present invention.

FIG. 4 is a block diagram of a circuit configuration of an image processing device according to a fourth embodiment. The difference between the fourth embodiment and the third embodiment is that, regarding a data item handled between the data sending/receiving units 7 and 7', the data item can be sent from the data sending/receiving unit 7 to the data sending/receiving unit 7', and that an output of a display output unit 9' is also connected to the display section 10.

Thus, an image data item that has been read from the memory section 14 by the reading section 12 and that is passed to the image-handling section 6' can be displayed again on the display section 10 by the display output unit 9'.

In the above-described embodiments, the correction process using a post-offset data item is described using an example in which the second image data item (I2−O3) shown in FIG. 5 is generated to correct an image data item. However, the correction process according to any of the embodiments of the present invention is not necessarily limited to the above-described process. For example, a method represented by {I2−(O2+O3)/2} may be used, in which the average of the pre-offset data item O2 and the post-offset data item O3 is subtracted from the image data item I2. Alternatively, a method represented by {I2−(W2·O2+W3·O3)} may be used, in which each of the pre-offset data item O2 and the post-offset data item O3 are multiplied by a weight W, and in which the offset data items multiplied by the weight W are subtracted from the image data item I2.

When offset data items are continuously read by the drive control section 5 at a plurality of times, a method may be used, in which, from among the continuously read offset data items, an offset data item that is read last and that has the least intense remaining afterimage is subtracted.

While the present invention has been described with reference to exemplary embodiments, it is to be understood that the invention is not limited to the disclosed exemplary embodiments. The scope of the following claims is to be accorded the broadest interpretation so as to encompass all modifications and equivalent structures and functions.

This application claims the benefit of Japanese Patent Application No. 2007-273513 filed Oct. 22, 2007, which is hereby incorporated by reference herein in its entirety.

What is claimed is:

1. An image processing device in a radiograph apparatus including a radiation detector, an image-data reading section configured to read an image data item stored in the radiation detector, an offset-data reading section configured to read offset data items from the radiation detector in a period in which radiation irradiation is not performed, and a control section configured to control the image-data reading section and the offset-data reading section, the image processing device comprising:

a data sending/receiving unit configured to send/receive data items from the image-data reading section and the offset-data reading section;

an image processing unit configured to generate a first image data item by subtracting a first offset data item read by the offset-data reading section from the image data item read by the image-data reading section, the first offset data item read before the image data item is read, and configured to generate a second image data item by subtracting a second offset data item read by the offset-data reading section from the image data item read by the image-data reading section, the second offset data item being read after the image data item is read;

a display unit configured to display the first image data item generated by the image processing unit; and a storage unit configured to store the second image data item generated by the image processing unit.

2. The image processing device according to claim 1, wherein the offset data items that have been read by the offset-data reading section are utilized for correction of the image data item read by the image-data reading section, the image data item read one of before and after the offset data items are read.

3. The image processing device according to claim 1, further comprising a reading unit configured to read the second image data item that is stored in the storage unit, wherein the display unit displays the second data item read by the reading unit.

4. A radiation image processing apparatus that performs correction for a radiation image detected from a radiation detector which is irradiated with radiation, the radiation image processing apparatus comprising:

a detecting unit configured to detect a first offset data item from the radiation detector before the radiation detector is irradiated with the radiation, configured to detect the radiation image from the radiation detector that is irradiated with the radiation, and configured to detect a second offset data item from the radiation detector after the radiation detector has been irradiated with the radiation; and a correction unit configured to correct the radiation image using the first offset data item when the radiation image is to be displayed on a display unit, and configured to correct the radiation image using the second offset data when the radiation image is to be recorded in a recording unit.

5. An image processing method comprising:

an image-data reading step of reading an image data item that is stored in a radiation detector;

an offset-data reading step of reading offset data items from the radiation detector in a period in which radiation irradiation is not performed;

a data sending/receiving step of sending/receiving data items obtained in the image-data reading step and the offset-data reading step;

an image processing step of generating a first image data item by subtracting an offset data item that has been read in the offset-data reading step from the image data item that has been read in the image-data reading step, the offset data item having been read before the image data item is read, and generating a second image data item by subtracting an offset data item that has been read in the offset-data reading step from the image data item that has been read in the image-data reading step, the offset data item being read after the image data item has been read;

a displaying step of displaying an image data item that has been generated in the image processing step; and a storing step of storing an image data item that has been generated in the image processing step, wherein the image data item that is displayed in the displaying step is the first image data item that has been generated in the image processing step, and the image data item that is stored in the storing step is the second image data item that has been generated in the image processing step.

6. A radiation image processing method for performing correction for a radiation image that has been detected from a radiation detector which is irradiated with radiation, the radiation image processing method comprising:

detecting a first offset data item from the radiation detector before the radiation detector is irradiated with the radiation, detecting the radiation image from the radiation detector that is irradiated with the radiation, and detecting a second offset data item from the radiation detector after the radiation detector has been irradiated with the radiation; and correcting the radiation image using the first offset data item when the radiation image is to be displayed on a display unit, and correcting the radiation image using the second offset data when the radiation image is to be recorded in a recording unit.

* * * * *